United States Patent [19]

Li

[11] Patent Number: 4,667,673

[45] Date of Patent: May 26, 1987

[54] ANASTOMOTIC DEVICE APPLICATOR AND METHOD

[75] Inventor: Lehmann K. Li, Fairfield, Conn.

[73] Assignee: American Cyanamid Company, Stamford, Conn.

[21] Appl. No.: 588,276

[22] Filed: Mar. 12, 1984

[51] Int. Cl.$^4$ .............................................. A61B 17/11
[52] U.S. Cl. ................................. 128/334 C; 128/346
[58] Field of Search ........... 112/334 C, 303 R, 334 R, 112/346

[56] References Cited

U.S. PATENT DOCUMENTS 3,771,526 11/1973 Rudie ................................ 128/334 C
4,055,186 10/1977 Leveen ............................. 128/334 C

FOREIGN PATENT DOCUMENTS 1057729 5/1959 Fed. Rep. of Germany ... 128/334 C
7711347 4/1979 Netherlands ..................... 128/334 C Primary Examiner—Michael H. Thaler
Attorney, Agent, or Firm—Charles F. Costello, Jr.

[57] ABSTRACT

An extension mounting apparatus on which a bowel anastomosis ring device may be mounted in prefixed position to facilitate handling, insertion and closure in bowel ends to be anastomosed may be advantageously removably attached to an inserter to provide an applicator which enables insertion in the bowel and manipulation from a point exterior of the area to be anastomosed so as to cause the bowel anastomosis ring device halves to become controllably connected to couple the bowel ends to be joined together in contiguous abutting relationship. A method of performing low colorectal anastomosis using the bowel anastomosis ring device and closing the mating ring halves by manipulating the applicator exteriorly of the anus involves passing the inserter portion of the applicator from the interior of the rectum to the exterior of the anus so that placement is always from the clean area of surgery and anastomosis to the dirty and contaminated end.

3 Claims, 16 Drawing Figures

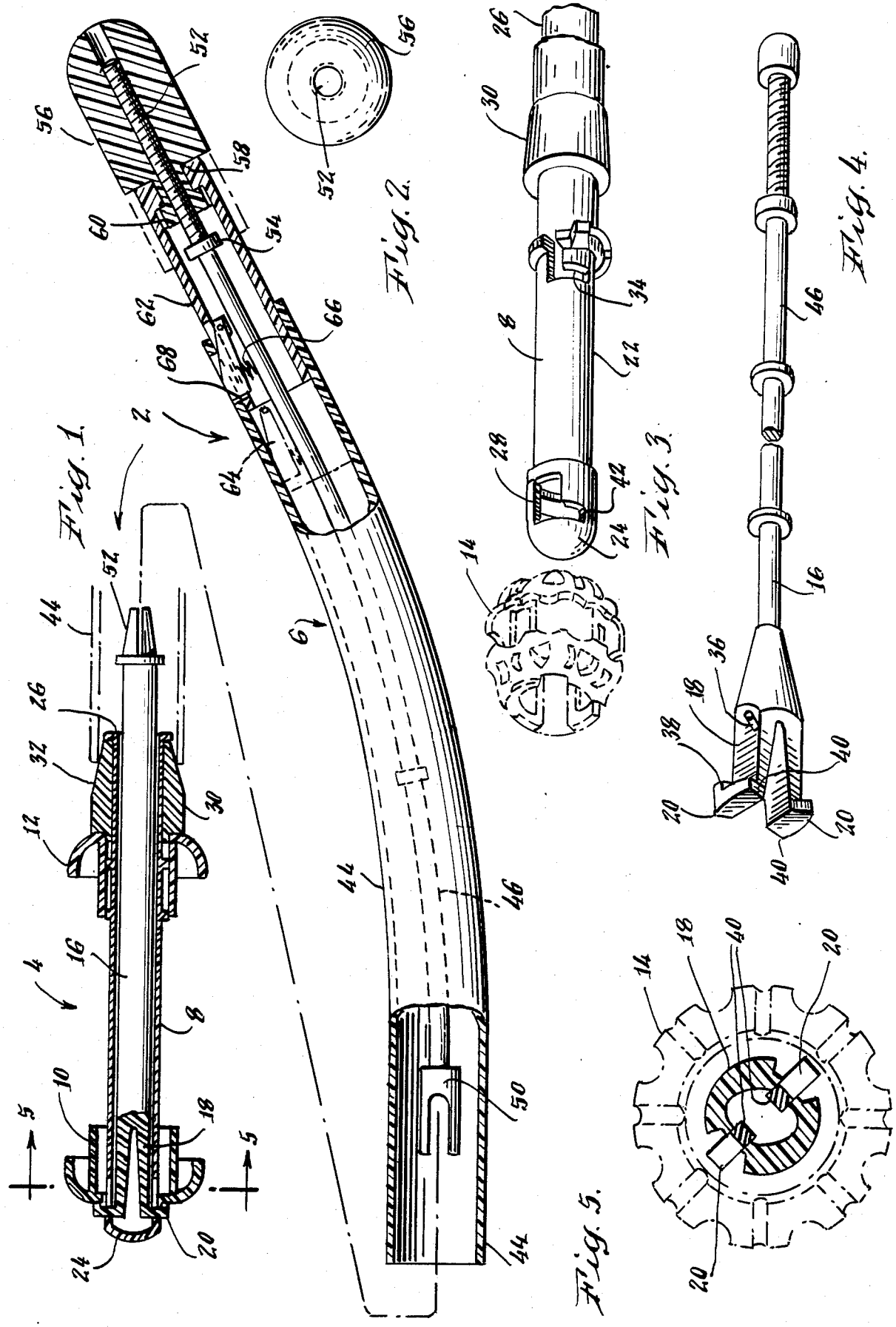

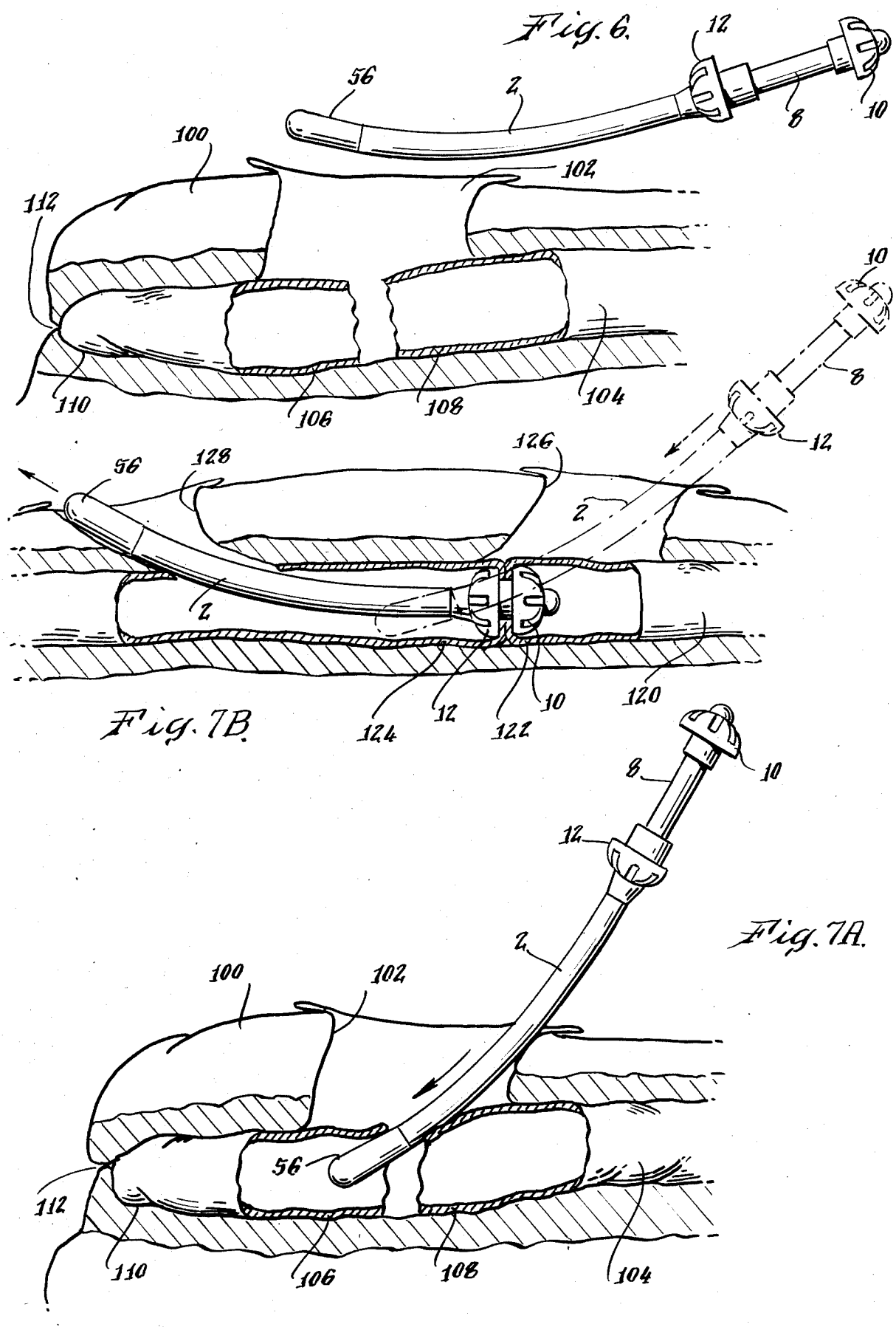

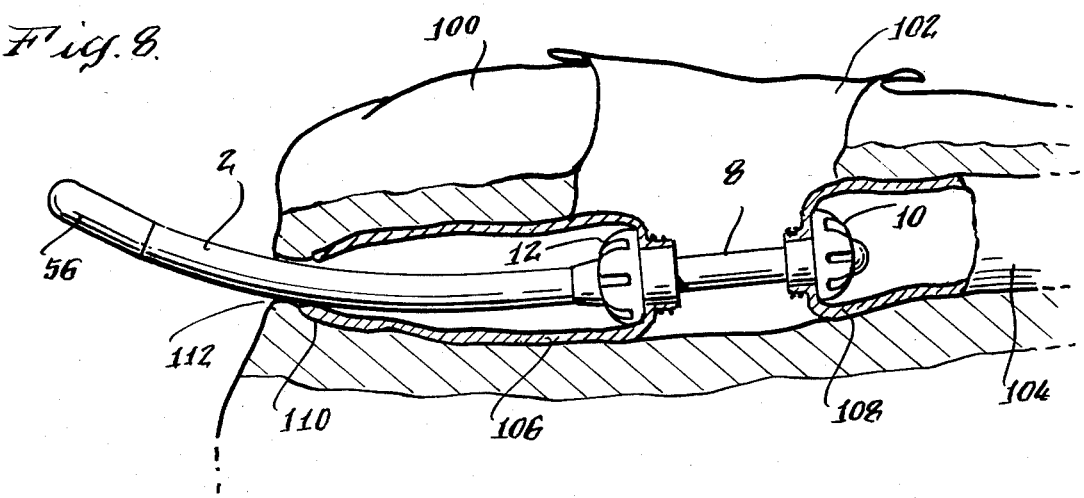
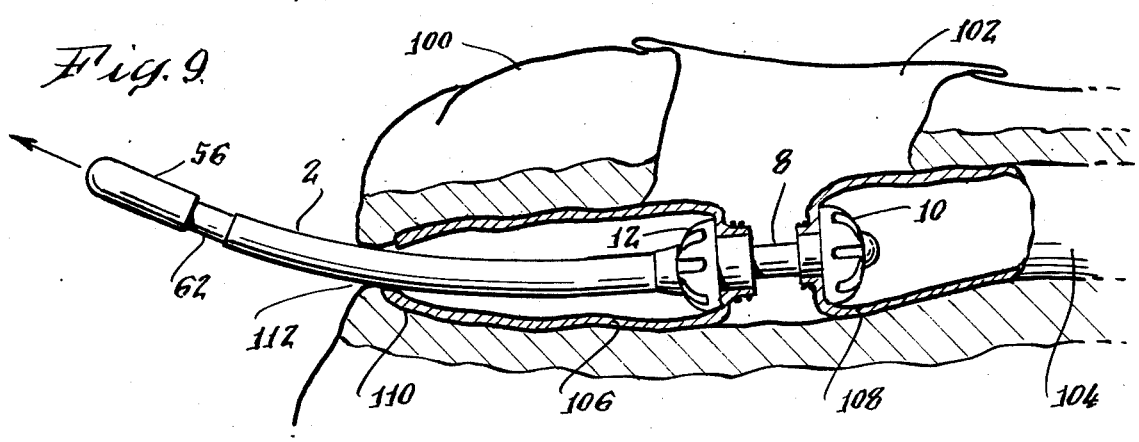
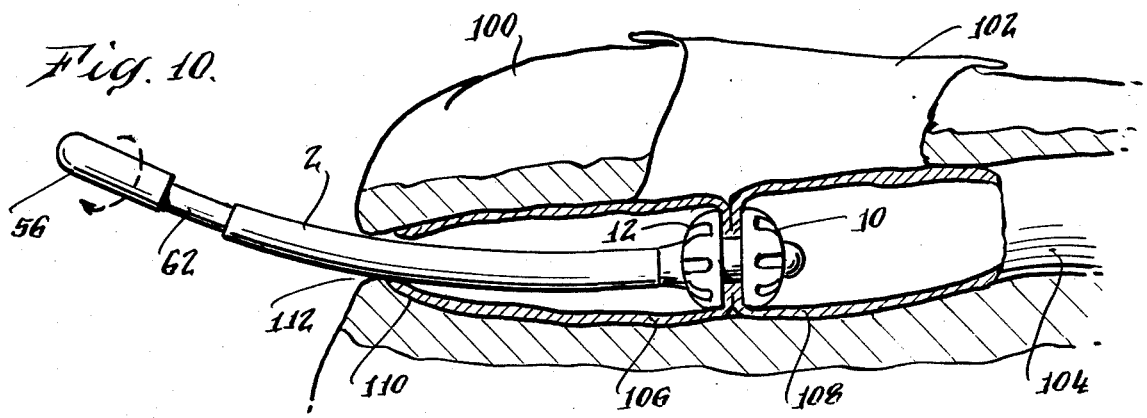
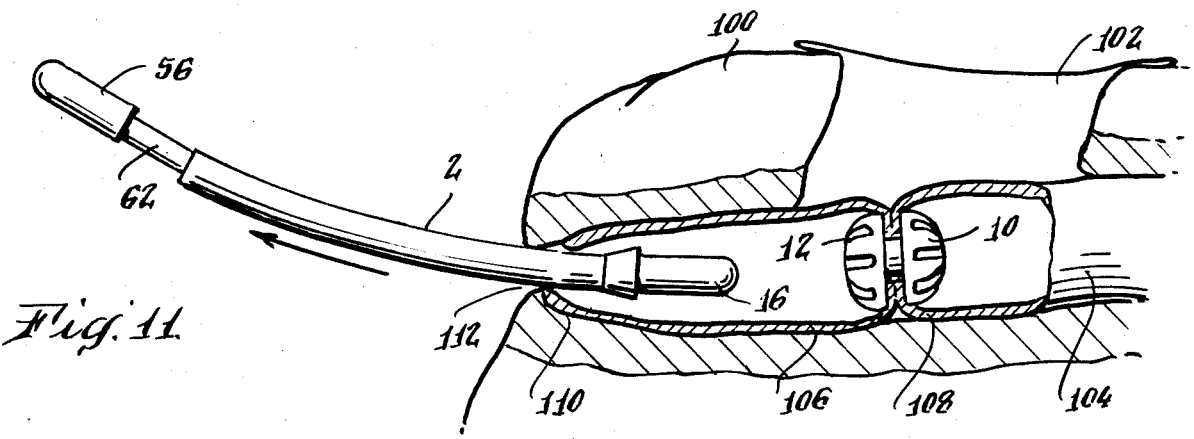

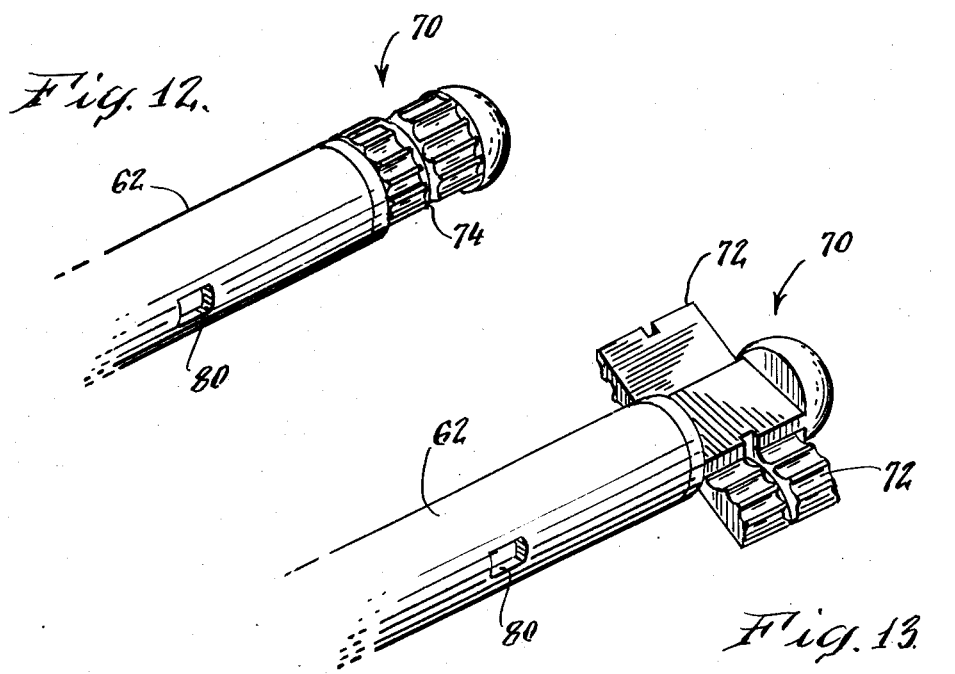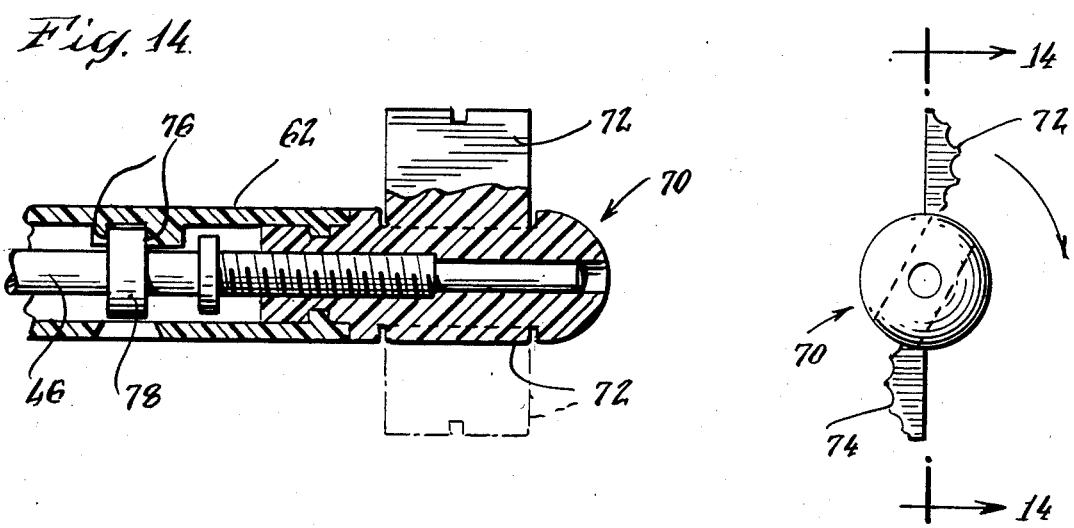

ANASTOMOTIC DEVICE APPLICATOR AND METHOD

BACKGROUND OF THE INVENTION

This invention relates to surgical devices, and, in particular, to a device and method for anastomosing tubular body members such as, for example, in connection with intestinal surgery.

Several procedures are known for anastomosing severed ends of tubular body structures such as the esophagus and the small and large intestines including suturing or clamping severed ends together or using stapling instruments. U.S. Pat. Nos. 4,304,236 and 4,319,576 disclose apparatus for circular surgical stapling of hollow organs.

A procedure for colorectal anastomosis using an end-to-end anastomosis stapler is disclosed in *Current Surgical Techniques,* Vol. 3, No. 3, Surgical Communications, Inc., Kenilworth, N.J. (1980). The instrument used, generally similar to those disclosed in the aforementioned patents, consists of a tubular housing with a central bore through which a rod is received for reciprocation by means of manually operable handles. A staple cartridge assembly, including staple and anvil carrying portions, is mounted on the housing at the end opposite the handles and is capable of firing circular rows of staples into evertically juxtaposed bowel ends for the anastomosis. The instrument is introduced into the bowel for positioning between the severed ends to be joined, either transanally or via a proximal colostomy that will subsequently be closed. For colorectal anastomosis, the transanal route is described as being preferred to obviate the need for making and closing a separate opening on the bowel. However, it is pointed out that such requires excellent mechanical preparation of the colon and rectum including purgation colonic lavage including saline washouts.

Anastomosis buttons and clamps are disclosed in U.S. Pat. Nos. 3,771,526, 4,055,186 and 4,154,241. These devices may utilize inserter rods which are forced upwardly into the rectum through the anus to position one-half of the clamp device in the lower colon and engage the other half positioned in the upper colon to draw the two together. Flexible fluid supply or drainage tubes to protrude through the anus may also be provided.

Technical difficulties in suturing techniques and inherent disadvantages of stapling instruments in anastomosis are also overcome by the inventions described in U.S. patent applications Ser. Nos., 198,448 abandoned and 287,500, U.S. Pat. No. 4,467,804 filed Oct. 20, 1980 and July 27, 1981, respectively, assigned to the assignee of the present application. Disclosed in those applications is an anastomotic device and method for receiving the free ends of an anatomic tubular structure to be anastomosed, respectively, over a pair of ring-like members having annular connecting means which mate with each other to connect the ring-like members. When the ring-like members are secured in a fixed relationship at a predetermined distance from each other, the free ends of the tubular members are clamped contiguous to each other to enable them to grow together and approximate the outer surface of the tubular member. The anastomosis device may be formed of disintegratable material to enable disintegration in the body.

In use, the device disclosed in those applications, which will be referred to hereinafter in its embodiment for use in the intestine as a bowel anastomosis ring device, is placed between the ends of the intestine to be joined together, the ends are pulled over the respective mating ring members and tightened using a purse string suture, so as to be turned inwardly, after which the ring members are urged together until connected with the intestine ends clamped in abutting relationship there between.

The present invention provides mounting and inserting applicator means to facilitate and enable more advantageous use of the bowel anastomosis ring device as well as a method for using the applicator means resulting in an improved surgical procedure for bowel anastomosis.

SUMMARY OF THE INVENTION

The invention provides an extension mounting means on which the bowel anastomosis ring device may be mounted in prefixed position to facilitate handling, insertion and closure in the bowel ends to be anastomosed. The extension may be advantageously removably attached to an inserter to provide an applicator which enables insertion in the bowel and manipulation from a point exterior of the area to be anastomosed so as to cause the bowel anastomosis ring device halves to become controllably connected to couple the bowel ends to be joined together in contiguous abutting relationship.

The applicator enables the surgeon to perform low colorectal anastomosis using the bowel anastomosis ring device and close the mating ring halves by manipulating the applicator exteriorly of the anus through which it is passed. However, an important distinction, as compared, for example, to stapling and prior clamping device procedures, it that the inserter portion of the applicator is passed from the interior of the rectum to the exterior of the anus so that placement is always from the clean area of surgery and anastomosis to the dirty and contaminated end.

An object of this invention is the provision of an anastomosis ring device mounting means.

Another object of this invention is the provision of an anastomosis ring device inserter enabling controllable closure of ring device halves to couple anatomic tubular ends together.

A further object of this invention is the provision of a method for bowel anastomosis using a clamping ring device mounted on an applicator which is placed from the clean area of surgery and anastomosis to the dirty and contaminated end.

In a preferred embodiment of the applicator of this invention, a smooth tubular outer member contains concentric therewith a shaft-like rod both of which are adapted to receive and interlock with a mounting extension containing the bowel anastomosis ring device ring halves to collectively provide an inserter for insertion in the upper half of the lower bowel and extension transanally. The extension mounting is also provided with an outer tubular member on which the ring halves are mounted and an inner tubular member containing a shaft-like rod concentric therewith. The rods of the extension mounting and the inserter are together movable linearly to draw the bowel anastomosis ring device halves together in gross adjustment. The rods are also movable with axial rotation translatable into linear motion for further closing of the ring halves in fine adjustment. These manipulations are achieved by rotating a knob-like extension of the inserter shaft rod exteriorly of the body. Upon complete closure, the shaft-like rod members can be manipulated, such as by counterclockwise rotation, to be disengaged from the bowel anastomosis ring halves so that the extension mounting together with the inserter may be withdrawn through the anus. In this manner, close control of the closing of the bowel anastomosis ring device to clamp the ends of the bowel to be joined together therebetween is achieved with minimum tissue trauma due to handling and with minimum contamination as a consequence of insertion from the bowel through the rectum and anus, that is, from the clean area to the dirty end.

Accordingly, a yet further object of this invention is the provision of a mechanical applicator means including a bowel anastomosis ring device extension mounting and an inserter which may be manipulated exteriorly of the body for controlled closure of the bowel anastomosis ring device to achieve a desired anastomosis.

The foregoing and other objects, advantages and features of this invention will be further apparent from the following description of preferred embodiments thereof having reference to the drawings included herewith and the claims appended hereto.

BRIEF DESCRIPTION OF THE DRAWINGS

FIG. 1 is a side view, partly in section, of an applicator showing the bowel anastomosis device mounting extension with the ring halves positioned thereon, and the inserter, also partly in section, with the dotted line showing the operative relationship between the two, according to an embodiment of this invention;

FIG. 2 is an end view of the applicator of FIG. 1;

FIG. 3 is a side view of the bowel anastomosis ring device shown in juxtaposition to the mounting extension to illustrate the manner in which the ring halves will be positioned thereon;

FIG. 4 is a side view of the rod-like shaft of the applicator of FIG. 1;

FIG. 5 is an end view, in section, taken along the line 5—5 of FIG. 1;

FIG. 6, 7A and 8 through 11 are schematic illustrations illustrating the use of the insertion device in a bowel anastomosis procedure according to an embodiment of this invention;

FIG. 7B is a schematic and phantom illustration showing the use and the direction for placement of the insertion device in a tubular anastomosis procedure according to an alternative embodiment of this invention;

FIG. 12 is a detailed view of the applicator knob;

FIG. 13 is a detailed view of the applicator knob having hinged-like grasping means according to an embodiment of this invention;

FIG. 14 is a sectional view, taken along the line 14—14 of FIG. 15, showing the manner in which the rod-like shaft is mounted in the applicator and details of the knob; and FIG. 15 is an end view of the applicator showing the knob portion.

DESCRIPTION OF THE PREFERRED EMBODIMENTS

Referring to FIG. 1, there is shown, in two parts, an anastomosis ring device applicator referred to generally at 2. The applicator includes a mounting extension 4 and an inserter 6. The mounting extension 4 is formed of a tubular housing 8 on which are positioned, at spaced-apart locations, respective mating halves, distal half 10 and proximal half 12, of a bowel anastomosis ring device, seen at 14 in FIG. 3. The bowel anastomosis ring device 14 is of the type described in U.S. patent application Ser. Nos. 198,448 and 287,500 filed Oct. 20, 1980 and July 27, 1981, respectively, referred to above. Slidably and rotatably positioned coaxially within the tubular housing 8 is a rod-like shaft 16, the distal end 18 of which is bifurcated and provided with holding tabs 20 the purpose of which will be described below.

As used herein, the term "distal" shall refer to that part of the applicator which is furthest away from the surgeon-user and the term "proximal" shall refer to that part of the applicator which is closest to the surgeon-user. The distal end will include the bowel anastomosis ring device while the proximal end will include the manipulation knob.

The tubular housing 8, seen also in FIG. 3, includes a generally cylindrical central portion 22 terminating in a closed end 24 and an open end 26. Proximate to the closed end 24 are two L-shaped openings 28, circumferentially diametrically opposed to one another, through which can project the tabs 20 of the shaft 16. Proximate the open end 26 the tubular housing 8 is surrounded by a collar 30 having a beveled portion 32 for tight fitting engagement into the opening of the inserter 6, as described hereinafter. Also located on the tubular housing 8 proximate to the collar 30 is a retaining curcumferential projection 32 for retaining the bowel anastomosis ring device half 12 in place on the housing 8. An L-shaped opening 34 is formed adjacent to the retaining ring 32 to receive the pin 36 on the bifurcated termination 18 of the rod 16 upon closure of the ring halves.

The holding tabs 20 of the rod-like shaft 16 extend through the respective openings 28 and engage, by means of the projection 38, the bowel anastomosis ring device ring half 10, as seen in FIG. 1. The tabs 20 can be caused to withdraw from the openings 28 by counterclockwise rotation within the tubular housing 8 by virtue of the cam surfaces 40 which cause the bifurcations of the end 18 and the tabs located thereon to be forced together so that they may be withdrawn from the openings 28 and fitted within the interior of the tubular housing 8. The cam surfaces 40 are formed and placed in relationship to the wall 42 of the opening 28 so as to be caused to be withdrawn upon counterclockwise revolution of the shaft 16.

The inserter 6 is formed of a tubular outer housing 44 and may be curved as shown in FIG. 1. The outer housing 44 is open at one end 46 to receive the beveled surface of the collar 32 when the inserter 6 and the mounting extension 4 are joined together. Slidably and rotatably positioned within the tubular housing 44 is a rod-like shaft 46 terminating at one end in a bayonet-type connection 50 which can form an interlock with complimentary portions 52 located on the shaft 16 of the mounting extension 4. The shaft 46 terminates at its other end in a threaded portion 52 and has spaced along its length circumferential spacers 54 to provide it with axial stability within the housing 44. A rotatable knob 56 is threaded on the end of the shaft portion 52 and is provided with a reduced diameter portion 58 having a circular flange 60 secured to a cylindrical housing 62 which is slidably positioned in the tubular housing 44. Pivotally mounted on the housing 62 is a button 64 biased by a spring 66 so that upon slidable movement the button 64 can be caused to project into the opening 68 cut into the curcumference of the housing 44.

The mechanical functioning of the applicator 2 is described as follows. The ring-like half members of the bowel anastomosis ring device, 10 and 12 respectively, are mounted on the extension 4 which is connected, through insertion of the collar portion 32 into the opening 46 of the inserter 6. An interlock is made between shafts 16 and 46 by means of members 52 and 50, respectively. The ring half 10 is held in place on the tubular housing 8 by the tabs 20 and the projections 38 and caused to move toward ring member 12 by linear movemet of the knob 56 such as by grasping and withdrawing it and cylindrical housing 62 from the housing 44 in the proximal direction. As the knob 56 is linearly retracted from the inserter housing 44, the shaft 46 is caused to move the shaft 16 of the extension mounting 4. This movement and the fact of the tabs 20 being positioned behind the ring half 10 cause the entire tubular housing 8 to move linearly with respect to the collar 32 and the ring member 12 and to be drawn concentrically into the interior space of the tubular housing 44.

After a predetemined linear movement, based on the anastomosis to be done, has been completed, the button 64 which has moved with the cylindrical housing 62 projects into the opening 68 of the housing 44 indicating that linear movement of the knob 56 is to cease. At this point, the ring halves 10 and 12 are close enough to one another for further approximation to be done by a more closely controlled movement. This is achieved by now rotating the knob 56 which, through the threaded engagement on the portion 52 of the shaft 46, causes the shaft 46 to move linearly in relationship to the rotational movement of the knob 56. This in turn causes the shaft 16 and tubular housing 8 to further draw the ring member 10 toward the half 12 until the two are engaged with one another. The tabs 20 can now be removed from their position behind the ring member 10 by a counter-clockwise movement of the knob 56 and hence of the rod 46 and rod 16 connected thereto to cause the cam surfaces 40 to strike the surfaces 42 in the openings 28 in the extension housing 8. This squeezes the bifurcations of the end 18 together for withdrawal through the interior of the housing 8 and 44. The entire extension mounting 4 and inserter 6 which together form the applicator 2 can then be withdrawn from the bowel anastomosis ring device 14.

An alternative embodiment of the knob is shown in FIGS. 12-14. Referring thereto, it is seen that the knob 70 is formed of two wing-like halves 72 having living hinges causing them to spring open when the band 74 holding them closed is released. FIG. 14 illustrates an alternative form for causing the controllable closing of the halves 10 and 12 by rotation of the wings 72. The housing 62 has fixed thereon a cam surface 76 along which travels the cam follower 78, a cylindrical projection on the rod shaft 46, in order to translate rotational movement of the rod 46 into linear movement and close the two halves 10 and 12 of the bowel anastomosis ring device. Instead of the button 64 indicating when the linear movement has resulted in the desired gross adjustment, a visual indicator resulting from a mark or color band on the shaft 46 can appear in the window 80.

FIGS. 6, 7A and 8 through 11 illustrate the use of the applicator device of FIG. 1 and the method of bowel anastomosis according to this invention. FIG. 7B illustrates the applicator device of FIG. 1 in a method of tubular anastomosis according to this invention. Although not critical to the practice of the method of tubular anastomosis, it is preferred that the incision 128 (i.e., not the incision 126) be the closest incision to the heart muscle, as this provides the maximum amount of arterial blood for healing. It is also to be understood that the use of the applicator for bowel anastomosis shown in FIGS. 8 through 11 describe identically the use of the application for tubular anastomosis except that the applicator is removed through the incision 128 instead of the rectum 110 and anus 112.

As described in the copending applications referred to above, the bowel anastomosis ring device consists of two identical halves of mushroom cap configuration which are caused to snap together, as shown at 14 in FIG. 3, thereby clamping sections of the bowel there between. According to this invention, the device can be used without the inserter 6. For example, the ring halves can be mounted on the extension mounting 4 in prefixed position and inserted between ends of the bowel to be anastomosed through a colostomy. Of course, the bowel anastomosis ring device can be used, as described in the copending applications referred to above, without either an extension mounting or inserter for anastomosis not requiring colostomy or transanal application. However, as illustrated in FIGS. 6, 7A and 8 through 11, the present invention makes possible a method for low anterior anastomosis utilizing transanal insertion proceeding from the clean surgical site to the dirty end to avoid contamination.

Referring generally to FIGS. 6 and 7A, there is schematically illustrated the applicator 2 and an abdomen 100 with an incision 102 therein providing access to the bowel 104 of which a diseased portion has been removed leaving lower bowel portion 106 and upper bowel portion 108. The lower bowel portion 106 communicates through the rectum 110 to the exterior of the body through the anus 112. FIG. 7A shows the applicator being placed in the opening of the lower bowel half 106.

FIG. 7B schematically illustrates the applicator 2 in place with a phantom illustration showing the placement of the applicator. The applicator is placed through an incision 126 which provides access to a tubular vessel 120 of which a diseased portion has been removed. This leaves a first tubular vessel portion 124 and a second portion 122. The first portion 124 communicates through the incision 128 to the exterior of the body. FIG. 8 shows the applicator 2 in place with the bowel halves 106 and 108 having been secured to the halves 12 and 10 of the bowel anastomosis ring device such as by purse string sutures.

FIG. 9 shows the knob 56 being linearly withdrawn, in the proximal direction, away from the inserter housing 6 and the body to cause the shaft 46 to move linearly to cause the tubular housing 8 of the extension mounting 4 to be withdrawn moving bowel anastomosis ring half 10 towards the other half 12, as described above. This is a gross adjustment. FIG. 10 illustrates the closure rod having been withdrawn to its fullest extension so that the two ring halves are brought into close approximation just prior to locking. The button or other indicator signals this position. At this point, the surgeon checks the proposed anastomosis and makes modifications as necessary. The bowel anastomosis ring device halves can be separated by merely reversing the linear direction of the closure rod so as to open the halves up.

If satisfactory, the applicator can now be activated for final closure of the two halves for engagement in place. This is achieved by rotating the knob 56, in the direction shown in FIG. 10, to translate the rotational movement, as previously described, into linear movement and controllably bring the two halves together for engagement. The applicator is then removed from the closed bowel anastomosis ring device by counterclockwise motion which disengages the tabs from the ring device and withdrawn from the body through the rectum and anus as shown in FIG. 11. This is done without obstruction or trauma to the anastomosis or distal colonic tissue.

It will be understood that the mounting extension 4 and inserter 6 can be made integral as one unit for certain situations of anastomosis of tubular body organs. However, an advantage of the embodiment shown is that the mounting extension 4 can be provided in a variety of sizes with the rings 10 and 12 prefixed thereon in different positions depending on the anastomosis to be achieved. The inserter 6 can be packaged separately to be useful with a variety of the mounting extensions 4.

Although a particular advantageous utility of the invention is in bowel anastomosis and with clamping ring devices used for such anastomosis, the device and method according to this invention may find utility in other types of anastomosis of tubular body members with appropriate adaptation for size and location involved. In addition, the method of this invention providing the new procedure of anastomosis by proceeding from the clean surgical site toward the dirty end when there is to be transanal insertion and manipulation outside of the body, can also find advantageous utility in anastomosis that utilize means other than clamping ring devices, such as stapling means which clamp the tubular members to be joined there between, and the like.

I claim:

1. In a method for surgically anastomosing tubular anatomic members including clamping the tubular anatomic members to be joined between mating halves of a clamping device and utilizing a longitudinal inserter inserted into at least one of the tubular members for positioning at least a portion of the clamping device for the anastomosis, the improvement comprising inserting the clamping device between the tubular anatomic members at the site of the desired anastomosis; causing the longitudinal inserter to extend into at least one of the tubular members by proceeding from the anastomosis site into the tubular member; and further causing the longitudinal inserter to project through an opening in the tubular member into which it is extended wherein the opening through which the inserter projects in a natural body orifice.

2. In a method for surgically anastomosing sections of the colon including clamping the colonic member to be joined between mating halves of a clamping device and utilizing a longitudinal inserter inserted into at least one of the members for positioning at least a portion of the clamping device for the anastomosis, the improvement comprising inserting the clamping device between the colonic members at the site of the desired anastomosis; causing the longitudinal inserter to extend into at least one of the members by proceeding from the anastomosis site into the tubular member; further causing the longitudinal inserter to project through an opening in the colonic member into which it is extended; and the mating halves of said clamping device come together by manipulating a shaft that draws at least one of said halves toward the other half, the means for manipulating said shaft located adjacent the proximal end of said shaft, wherein the clamping device is a bowel anastomosis ring device having ring-like halves and at least one-half is mounted on an applicator, the applicator is caused to enter into the lower colon portion from the site of the anastomosis, through the rectum and out of the anus and the ring halves are caused to come together by manipulating the applicator exteriorly of the anus.

3. A method for surgically anastomosing sections of the colon as claimed in claim 2 wherein said manipulating means are separable from said shaft.

* * * * *